United States Patent
Rangan et al.

(10) Patent No.: US 10,843,240 B2
(45) Date of Patent: Nov. 24, 2020

(54) MULTIFUNCTIONAL STORAGE CONTAINER FOR PERISHABLE PRODUCTS AND SOLID WASTE

(71) Applicant: MATERIALS MODIFICATION INC., Fairfax, VA (US)

(72) Inventors: Krishnaswamy Kasthuri Rangan, Fairfax, VA (US); Tirumalai Srinivas Sudarshan, Vienna, VA (US)

(73) Assignee: MATERIALS MODIFICATION INC., Fairfax, VA (US)

( * ) Notice: Subject to any disclaimer, the term of this patent is extended or adjusted under 35 U.S.C. 154(b) by 355 days.

(21) Appl. No.: 15/905,700

(22) Filed: Feb. 26, 2018

(65) Prior Publication Data
US 2018/0243807 A1 Aug. 30, 2018

Related U.S. Application Data

(60) Provisional application No. 62/464,157, filed on Feb. 27, 2017.

(51) Int. Cl.
| | |
|---|---|
| B09B 3/00 | (2006.01) |
| A61L 2/04 | (2006.01) |
| B65D 81/28 | (2006.01) |
| B65D 33/00 | (2006.01) |
| A61L 11/00 | (2006.01) |
| B65D 81/18 | (2006.01) |
| B65F 7/00 | (2006.01) |
| B65D 81/34 | (2006.01) |
| B65F 1/00 | (2006.01) |
| A61L 2/18 | (2006.01) |

(52) U.S. Cl.
CPC .............. *B09B 3/0083* (2013.01); *A61L 2/04* (2013.01); *A61L 2/18* (2013.01); *A61L 11/00* (2013.01); *B09B 3/0025* (2013.01); *B65D 33/00* (2013.01); *B65D 81/18* (2013.01); *B65D 81/28* (2013.01); *B65D 81/34* (2013.01); *B65F 1/0006* (2013.01); *B65F 7/00* (2013.01)

(58) Field of Classification Search
CPC ........ B09B 3/0025; B09B 3/0083; A61L 2/04
See application file for complete search history.

(56) References Cited

U.S. PATENT DOCUMENTS

| | | | |
|---|---|---|---|
| 5,908,649 A | 6/1999 | Floyd | |
| 9,114,929 B2 | 8/2015 | Gurp | |
| 2018/0319569 A1* | 11/2018 | McGoff | ............. B65D 81/3897 |

OTHER PUBLICATIONS

Balasubramaniam, R, Hegde, U, and Gokoglu, S, Analysis of Water Recovery Rate From the Heat Melt Compactor, NASA Technical Memorandum, NASA/TM-2013-216573, Document ID 20140011480 (2013).

Cucinotta, FA, Kim, MHY, Chappell, LJ, Evaluating shielding approaches to reduce space radiation cancer risks, NASA Technical Memorandum—2012-217361 (2012).

(Continued)

*Primary Examiner* — Kevin Joyner
(74) *Attorney, Agent, or Firm* — Jyoti C Iyer

(57) ABSTRACT

Disclosure of a container to store solid and liquid wastes and perishable goods and protect them from microbial damage. The storage container is also amenable to selectively remove water vapor from inside the bag without damaging the container.

5 Claims, 6 Drawing Sheets

(56) References Cited

OTHER PUBLICATIONS

Fisher, JW, and Lee, JM, Space Mission Utility and Requirements for a Heat Melt Compactor, 46th International Conference on Environmental Systems ICES-2016-37710-14, Jul. 2016, Vienna, Austria.

Turner, MF, Fisher, JW, Broyan. J, and Pace, G, Generation 2 Heat Melt Compactor Development, 44th International Conference on Environmental Systems ICES-2014-024 13-17 Jul. 2014, Tucson, Arizona.

Strayer, RF, Hummerick, ME, Richards, JT, McCOY, LE, Roberts, MS, and Wheeler, RM, Microbial Characterization Space Solid Wastes Treated with a Heat Melt Compactor, 42nd International Conference on Environmental Systems, Jul. 15, 2012-Jul. 19, 2012, San Diego, CA, Document ID 20120008327.

Mitshuishi, K, Komada, S, and Kawasaki, H, Mechanical properties of oriented porous polypropylene filled with modified calcium carbonate, Journal of Materials Science Letters, 6: 434-436 (1987).

Green, DL, McAmish, L, McCormick, AV, Three-dimensional pore connectivity in bi-axially stretched microporous composite membranes, Journal of Membrane Science, 279:100-110 (2006).

Wagner, GW, Koper, OB, Lucas, E, Decker, S, and Klabunde, KJ, Reactions of VX, GD, and HD with Nanosize CaO: Autocatalytic Dehydrohalogenation of HD, Journal of Physical Chemistry B 104; 5118-5123 (2000).

Kleinhammes, A, Wagner, GW, Kulkarni, H, Jia, Y, Zhang, Q, Qin, L-C, WU, Y, Decontamination of 2-chloroethyl ethyl sulfide using titanate nanoscrolls, Chemical Physics Letters, 411: 81-85 (2005).

Khaleel, A, LI, W and Klabunde, KJ, Nanocrystals as stoichiometric reagents with unique surface chemistry. New adsorbents for air purification, Nanostructured Materials, 12: 463-466 (1999).

Klabunde, KJ, Stark, J, Koper, O, Mohs, C, Park, DG, Decker, S, Jiang, Y, Lagadic, I, and Zhang, D, Nanocrystals as Stoichiometric Reagents with Unique Surface Chemistry, Journal of Physical Chemistry 100: 12142-12153 (1996).

Wagner, GW, Procell, LR, O'Connor, RJ., Munavalli, S, Carnes, CL, Kapoor, PN, Klabunde, KJ, Reactions of VX, GB, GD, and HD with Nanosize $Al_2O_3$. Formation of Aluminophosphonates, Journal of American Chemical Society 123:1636-1644 (2001).

Vorontsov, AV, Savinov, EN, Davydov, L, and Smirniotis, PG, Photocatalytic Destruction of Gaseous Diethyl sulfide over $TiO_2$, Applied Catalysis B: Environmental, 32: 11-24 (2001).

Kozlov, DV, Vorontsov, AV, Smirniotis, PG, and Savinov, EN, Gas-phase photocatalytic oxidation of Dimethylsulfide over $TiO_2$: Kinetic Investigations and Catalyst Deactivation, Applied Catalysis B: Environmental, 42: 77-87 (2003).

Sun, X, and Li, Y, Synthesis, and Characterization of Ion-Exchangeable Titanate Nanotubes, Chemistry European Journal, 9: 2229-2238 (2003).

* cited by examiner

MULTIFUNCTIONAL STORAGE CONTAINER FOR PERISHABLE PRODUCTS AND SOLID WASTE

RELATED APPLICATIONS

This Application claims the benefit of U.S. Provisional Appl. No. 61/464,157, filed Feb. 27, 2017, which is incorporated in entirety by reference.

STATEMENT REGARDING FEDERALLY SPONSORED RESEARCH OR DEVELOPMENT

This invention was made with government support under SBIR contract numbers, NNX16CA47P and NNX17CA07C, awarded by NASA. The government has certain rights in the invention.

FIELD

This disclosure relates to a multifunctional storage bag for perishable products and solid wastes.

This disclosure provides a multifunctional storage bag with water vapor permeability and antimicrobial property and ambient temperature and water vapor impermeability and antimicrobial property when heated above 120 degrees C.

This disclosure provides a waste storage bag for solid and liquid wastes.

This disclosure provides a storage container to recover water from the waste without breaking or disintegrating the container.

This disclosure provides a storage container to protect the compacted trash from microbial infestation.

This disclosure provides a storage container for trash which is also amenable to radiation shielding.

This disclosure provides a storage container to protect perishable food, vegetables, fruits, and goods from damage and protect from microbial growth.

This disclosure provides a storage container to protect plant and tree roots of and saplings from drying during transport.

This disclosure provides a storage container that creates atmosphere for ripe fruits and vegetables faster.

BACKGROUND

The Environmental Control and Life Support System (ECLSS) for the International Space Station (ISS) handles all types of solid, liquid and gaseous wastes. The function of ECLSS is to provide the crew with a comfortable environment. The waste management is a critical part of the ECLSS (http://www.nasa.gov/sites/default/files/104840main_e-clss.pdf).

In the Shuttle missions, waste was collected and manually compressed to reduce storage volume. All wet and dry trash generated in the space shuttle was returned to Earth for disposal. On the ISS, wet and dry trash is collected in separate containers. It is either sent back to Earth with a visiting crew or placed into a Progress rocket and subsequently burned upon reentry. However, these approaches are not viable for longer duration missions.

NASA has developed a waste management device called the Heat Melt Compactor (HMC) as part of the Advanced Exploration Systems (AES) Human Spaceflight Logistics Reduction and Repurposing (LRR) project (R. Balasubramaniam, U. Hegde S. Gokoglu, Analysis of Water Recovery Rate From the Heat Melt Compactor, NASA Technical Report TM—2013-216573).

Human space missions generate a significant amount of trash. The plastic rich trash contains valuable water trapped in food residue, wipes, paper, duct tape, rubber gloves, and other miscellaneous trash items. The Heat Melt Compactor was designed to provide high trash volume reduction, microbial stabilization, and resource recovery including water and potentially create radiation shielding materials from the trash (Evaluating Shielding Approaches to Reduce Space Radiation, Retrieved from http://three.jsc.nasa.gov/articles/CucinottaKim Chappell0512.pdf).

The materials most commonly used now for garbage bags and trash containers, both in the civilian domains and for specialized NASA applications, include Low-Density Polythene (LDPE), High-Density Polythene (HDPE), recycled polythene, liner blend polythene, Medium Density Polythene (MDPE), Metallocene Polythene (mPE), degradable polythene, woven polypropylene, biodegradable polythene, and co-extruded plastic bags. These materials meet FDA and USDA specifications of low cost, hygiene, leak resistance, light weight, durability, portability, and recyclability. These bags and containers take up considerable storage space, more so in long duration missions and in the International Space Station (J. W. Fisher, J. M. Lee, Space Mission Utility and Requirements for a Heat Melt Compactor, $46^{th}$ International Conference on Environmental Systems (2016)).

The Heat Melt Compactor dries, compresses, and encapsulates the waste inside the plastic producing a tile (or disk) that has the consistency of hard plastic. Increasing the amount of space volume available in the crew habitat is highly beneficial for long duration flight missions. The trash accumulated from food and supplies occupy lots of valuable space in the spacecraft. Reduction of the volume occupied by trash using the HMC will enable the recovery of precious space in the crew compartment by more than 85 percent (M. F. Turner, J. W. Fisher, J. Broyan, G. Pace, 44th International Conference on Environmental Systems ICES-2014-024 13-17 Jul. 2014, Tucson, Ariz. Generation 2 Heat Melt Compactor Development).

Water from the trash is captured and reclaimed by the water removal subsystem of HMC. The trash along with the container is partially compressed and heated. The steam or water vapor that was produced was collected through a baffled chamber. The water collection system is currently functioning in a 1 g environment, and a separate effort is underway to operate the HMC in a microgravity environment.

There is a concern that the heat melt compacted processed disk surfaces may be susceptible to microbial attack during long-term storage. Therefore, the growth of pathogens on the HMC processed disk surfaces should be retarded by an antimicrobial agent from the trash bag (R. F. Strayer, M. E. Hummerick, J. T. Richards, R. M. Wheejer, L. E. McCol, and M. S. Roberts, Microbial Characterization Space Solid Wastes Treated with a Heat Melt Compactor, Retrieved from ntrs.nasa.gov/archive/nasa/casi.ntrs.nasa.gov/20120008327.pdf).

In the Gen-2 HMC operation, the trash undergoes several stages of processing. First, the trash undergoes low-temperature heating of 70-100 degrees C. to heat the trash and boil off most of the water that is loosely bound to the trash. This stage takes 2-4 hours. The second stage of the process dries and sterilizes the trash at an elevated temperature of approximately 150 degrees C. for 3-5 hours. The final stage is the cooldown of the trash tile. The complete cycle including heating, sterilizing, and cooling of the trash tile has been calculated to be approximately 12 hours. Some of the shortcomings of the current processing cycle followed by NASA are as follows:

As trash is heated in the compaction chamber, various volatile compounds are released into the effluent gas stream along with vaporized water. Therefore, the water recovered from trash is highly contaminated with organics.

The trash is wet and contaminated with microorganisms which can escape with water vapor.

Plugging of the vents on the compaction chamber occur due to melted plastic or trash deposition on the vents.

The inventive multifunctional waste disposal bags have several advantages to overcome these limitations.

The hydrophilic polymer gel is selectively permeable to water vapor and can retard the permeation of the organic contaminants.

Antimicrobial Ag—CuO is capable of neutralizing microbes escaping the trash bag during water recovery and compaction processing.

Waste disposal bags are made up of high-temperature stable polymers, and will not melt and plug the vents, unlike polyethylene bags that are currently used.

Waste disposal bags also will encapsulate melting trash goo and stop the plugging of vents.

The function of HMC such as reduction in the volume of the solid waste, disinfection/sterilization of the trash, recovering water.

Water Removal and Recovery

Removing the water from trash makes the condensed water available for recycling, and it dries the trash. Dry trash is crucial because it does not support the growth of microorganisms. Microbes do not grow on substances if the material is at a water activity of less than about 0.6. (Water activity is the partial vapor pressure of water in a substance divided by the standard state partial vapor pressure of water). Therefore, it is critical to remove water from the trash-compacts and goal of this task will be to achieve water activity levels below 0.6.

SUMMARY

The disclosed teachings provide making of a storage container based on porous polymer sheet coated or laminated with a hydrophilic polymer layer.

The disclosed teachings provide making of a storage container based on porous polymer sheet filled with an antimicrobial agent and a hydrophilic polymer.

The disclosure provides a storage container with water vapor permeability and antimicrobial properties.

The present invention relates to a composite sheet material that is water vapor permeable and substantially liquid water impermeable. The composite sheet has a water vapor transmission rate of greater than 1000 g/m²/day when measured according to standard ASTM E-96 Water method at 35 degree C.

The disclosure provides a flexible water vapor permeable, antimicrobial storage bag having an outer multifunctional layer and a porous inner support layer. The outer multifunctional layer includes a hydrophilic polymer and an antimicrobial agent. The outer multifunctional layer can be a coating or a sheet with the components of the outer multifunctional layer. The hydrophilic polymer can be polyvinyl alcohol or polyvinyl pyrrolidone. The antimicrobial can be silver doped copper oxide, magnesium hydroxide, copper-doped magnesium hydroxide, silver doped magnesium hydroxide, magnesium oxide, copper doped magnesium oxide, silver doped magnesium oxide, titanium dioxide nanotubes, or silver and copper ion exchanged titanium dioxide nanotubes. The porous inner support layer is a porous polymer sheet which can be polypropylene, nylon, polyester, polyurethane, polyimide, polytetrafluoroethylene or polyetherimide. The hydrophilic polymer behaves as an adhesive at a temperature higher than about 120 degrees centigrade and fills up and closes pores in the porous inner support layer. Inserting a waste material into the flexible, water vapor permeable, antimicrobial storage bag, then sealing the storage bag to encapsulate the waste material, applying vacuum and heating up to 120 degrees centigrade allows recovery of water vapor. Heating to higher than 120 degrees centigrade configures the flexible, water vapor permeable, antimicrobial storage bag to a substantially water vapor impermeable, antimicrobial product. The flexible, water vapor permeable, antimicrobial storage bag is sealed on all sides except providing an opening to receive a waste material. The substantial water vapor impermeable, antimicrobial product is pressure compressible into a sealed disc. The compression of the storage bag containing waste material does not cause disintegration of the storage bag, i.e. the storage bag maintains its integrity when heated to higher than 120 degrees centigrade under vacuum and undergoing compression. The flexible, water vapor permeable, the antimicrobial storage bag is impermeable to liquid water at room temperature and at temperatures of up to 120 degrees centigrade and higher.

The disclosure provides methods of using a storage bag to recover water vapor from the waste material while providing water vapor impermeability and antimicrobial property useful for storage of waste material within the storage bag. In some methods, a flexible water vapor permeable antimicrobial storage bag is prepared. Then a waste material is inserted into the storage bag through an opening in the storage bag. Then the opening in the storage bag is sealed, and vacuum is applied along with heating upto 120 degrees centigrade to recover water vapor from the contents of the storage bag. Then the heating temperature is raised to higher than 120 degrees centigrade to create a substantial water vapor impermeable antimicrobial heat treated product. The heating extracts out water vapor and makes the storage bag substantially liquid water impermeable. Preparation of storage bag includes coating an outer multifunctional layer onto a porous inner support layer to obtain a multilayer sheet. The outer multifunctional layer includes a hydrophilic polymer and an antimicrobial agent. The hydrophilic polymer can be polyvinyl alcohol or polyvinyl pyrrolidone. The antimicrobial can be silver doped copper oxide, magnesium hydroxide, copper-doped magnesium hydroxide, silver doped magnesium hydroxide, magnesium oxide, copper doped magnesium oxide, silver doped magnesium oxide, titanium dioxide nanotubes, or silver and copper ion exchanged titanium dioxide nanotubes. The porous inner support layer includes a porous polymer sheet which can be polypropylene, nylon, polyester, polyurethane, polyimide, polytetrafluoroethylene, or polyetherimide. The hydrophilic polymer behaves as an adhesive at a temperature higher than about 120 degrees centigrade and fills up and closes pores in the porous inner support layer. The water vapor permeable, the antimicrobial storage bag is flexible and includes an open section to receive waste material. Further, the substantially water vapor impermeable antimicrobial heat treated product can be compressed to obtain compressed, liquid water impermeable, antimicrobial product which encapsulates and completely covers the waste material.

In some embodiments, the storage bag is prepared by laminating a porous inner support layer with an outer multifunctional sheet to obtain a multilayer sheet.

BRIEF DESCRIPTION OF FIGURES

The above objectives and advantages of the disclosed teachings will become more apparent by describing in detail preferred embodiments thereof with reference to the attached drawings in which.

DETAILED DESCRIPTION

The disclosure relates to a multifunctional storage container which could be a pouch, bag, tube, or wrap capable providing both water vapor permeability and antimicrobial property at ambient conditions and provide water vapor barrier and antimicrobial property when heated to a temperature above 120 degree C.

Figure 1:
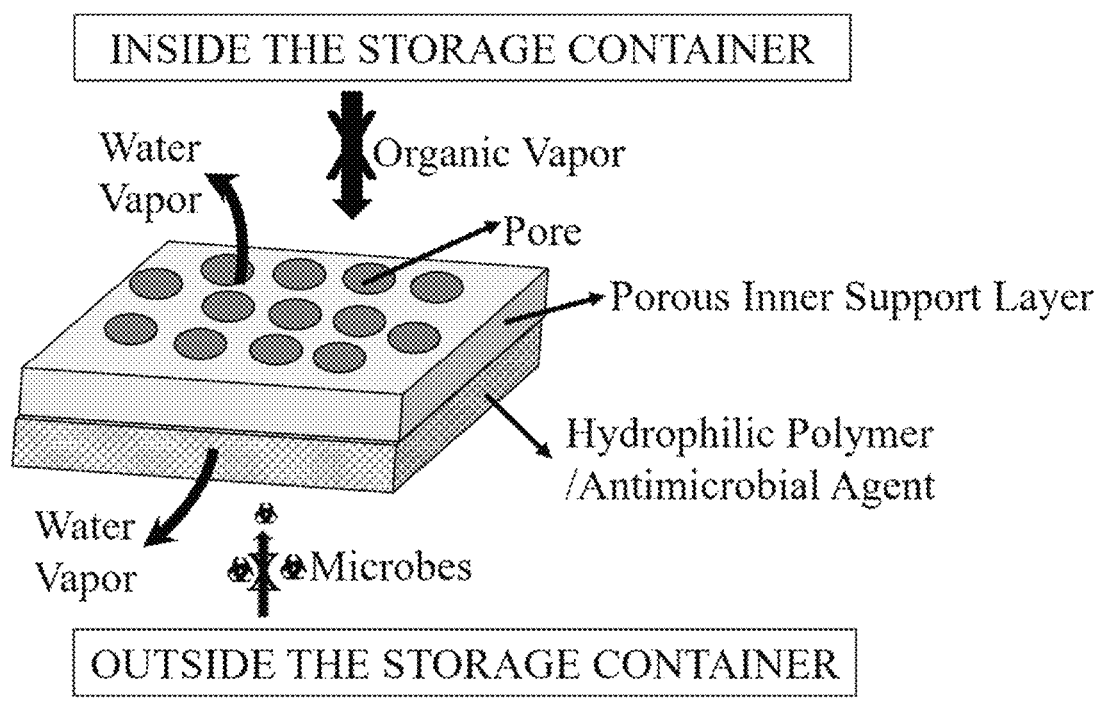
FIG. 1 provides a schematic diagram of multilayer material showing porous polymer inner support layer and outer multifunctional layer. Outer multifunctional layer includes hydrophilic polymer and antimicrobial agent.

Polymer sheets with nano and micro-sized pores provide a platform to design membranes with useful properties and applications. Filling the pores and coating of the porous polymer sheet with a hydrophilic polymer or hydrophilic polymer gel results in polymer composite sheets, where the filler can enhance or regulate the transport of specific substances in the desired direction. Compared to dense membranes, these composite polymer sheets can be tailored to the type of filler, coating material, pore size, and porosity of the membrane to provide tunable vapor transport properties. A schematic representation of the multilayer sheet material is provided in FIG. 1.

The host porous polymer sheet provides a mechanically strong, durable, flexible barrier while the filler within the pores and coating on top of porous polymer inner support layer provides selective water vapor transport while retarding organic vapor along with antimicrobial properties. The pores within the inner support porous polymer sheet were filled with a mixture of hydrophilic polymer (for example, polyvinyl alcohol (PVA and Polyvinylpyrrolidone, PVP) and an antimicrobial inorganic silver doped metal oxide (Ag—CuO) or) or coated with a mixture of hydrophilic polymer (for example, polyvinyl alcohol (PVA, and Polyvinylpyrrolidone, PVP) and an antimicrobial inorganic silver doped metal oxide (Ag—CuO). This multifunctional polymer layer will provide the dual functionality of allowing water vapor to escape from the storage bag while retarding the growth of harmful pathogens. The bag will also reduce the toxic organic chemical vapors or liquids diffusing out the of the bag.

Microporous polymer membranes with interconnected networks of pores are fabricated by melting and stretching of calcium-carbonate-compounded-polyolefins (K. Mitshuishi, S. Komada, H. Kawasaki, Mechanical properties of oriented porous polypropylene filled with modified calcium carbonate, J. Mater. Sci. Lett. 6, 434 (1987)). This type of material is relatively cheap and is commercially available in bulk quantities. It can encapsulate solids but permit the passage of water vapor. It is most often employed as breathable diaper-back sheets, which have recently revolutionized the production of disposable diapers. Breathable microporous membranes are also used in surgical gowns and other medical fabrics, acting as a barrier to blood and other bodily fluids that can transmit infectious diseases to patients and healthcare workers. Recent studies have shown that these materials possess pores that are three-dimensionally (3D) interconnected, and exhibit WVTR of 1000-5000 $g/m^2/day$, which are in the breathable range (D. L. Green, L. McAmish, A. V. McCormick, Three-dimensional pore connectivity in bi-axially stretched microporous composite membranes, Journal of Membrane Science, 279, 100-110 (2006)).

The water vapor diffusion in these microporous membranes seems to follow the Fickian diffusion model, where the mean free path is of the order of 0.05 µm (the average distance that a water molecule travels between collisions) and is much shorter than the dimensions of the pore (1 micrometer).

Microporous film laminates are porous membranes (pore size 0.1-50 micrometer) that are coated onto fabric. The most widely used are polyolefins, polyurethanes, polytetrafluoroethylenes, acrylics, and poly amino acids. In one such fabric manufactured by Pragma Corporation, Colmar, Pa. a porous, vapor-permeable polyethylene membrane is laminated to a polypropylene spun bond. Spunbond is a nonwoven material made of long continuous fibers that are stretched upon extrusion, resulting in the strong machine direction and transverse direction.

Water vapor transport rate data showed that the WVTR value decreases upon polymer gel infiltration as expected. However, both polymer-gel-filled and CuO/polymer-gel-filled exhibited closer WVTR values (>1000 $g/m^2/day$). It is important to note that these values are measured at room temperature (25 degree C.). At higher temperatures (upto 120 degree C.) WVTR values will be much higher reaching about 2 to 5 orders of magnitude compared to room temperature data.

PVP and PVA are hydrophilic polymers and have high thermal stability (Melting point >100 degree C.). PVP and PVA are considered safe in many applications by the U.S. Food and Drug Administration (FDA). It is commonly used in hair gels, as binders in pharmaceutical tablets and textile dyeing and most importantly as a hot-melt adhesive (hot glue stick). Hydrophilic polymer layer will allow water vapor to escape the trash bag and function as a melt adhesive that will seal the solid waste after water removal during HMC processing (J. W. Fisher, J. M. Lee, Space Mission Utility and Requirements for a Heat Melt Compactor, 46th International Conference on Environmental Systems (2016)).

Use of solid decontaminating media for the clean-up of hazardous waste pollutants depends on the reactivity of the solid particles. Once trapped within the solid, the toxic agent decomposes that and renders it harmless. Earlier studies have proven the decontamination properties of nanopowders of MgO, CaO, Alumina, and Titania. All these oxides in the nanocrystalline form were shown to decontaminate chemical agents, at different rates. Several nanocrystalline adsorbent materials including $Mg(OH)_2$, Cu-doped $Mg(OH)_2$, Ag-doped $Mg(OH)_2$, MgO, Cu-doped MgO, Ag-doped MgO, and $TiO_2$ nanotubes, silver, and copper ion-exchanged $TiO_2$ nanotubes. These materials exhibited strong antimicrobial and toxic chemical decontamination properties. It is important to note here that unlike organic molecule-based antimicrobial agents, inorganic metal oxides will not decompose or deactivate during the high-pressure/high-temperature HMC process (Wagner, G. W; Koper, O. B; Lucas, E; Decker, S; Klabunde, K. J; J. Phys. Chem. B 104; 5118 (2000); Kleinhammes, A; Wagner, G. W; Kulkarni, H; Jia, Y; Zhang, Q; Qin, L-C; Wu, Y; Chemical Physics Letters 411 81-85 (2005); Khakel, W. Li, and K. J. Klabunde, Nanocrystals as stoichiometric reagents with unique surface chemistry. New adsorbents for air purification, Nanostructured Materials, 12, 463-466, (1999); Klabunde, K. J; Stark, J; Koper, O; Mohs, C; Park, D. G; Decker, S; Jiang, Y; Lagadic, I; Zhang, D; J. Phys. Chem. 100; 12142 (1996); G. W. Wagner, L. R. Procell, R. J. O'Connor, S. Munavalli, C.L. Carnes, P. N. Kapoor, K. J. Klabunde, J. Am. Chem. Soc. 123; 1636 (2001); A. V. Vorontsov, E. N. Savinov, L. Davydov, P. G. Smirniotis, Photocatalytic Destruction of Gaseous Diethyl sulfide over TiO2, Applied Catalysis B: Environmental, 32; 11-24 (2001); D. V. Kozlov, A. V. Vorontsov, P. G. Smirniotis, E. N. Savinov, Gas-phase photocatalytic oxidation of Dimethylsulfide over TiO2: Kinetic Investigations and Catalyst Deactivation, Applied Catalysis B: Environmental, 42, 77-87 (2003); X. Sun and Y. Li, Synthesis, and Characterization of Ion-Exchangeable Titanate Nanotubes, Chem. Eur. J., 9, 2229-2238 (2003)).

The polymer composite membranes also have the added advantage as a radiation shielding material. It is the primary issue of NASA to protect astronauts from GCR and SPEs during long-duration space missions. "Comparisons of liquid hydrogen, polyethylene, water, and epoxy shielding to aluminum show that statistically significant improvements in GCR risk reduction relative to aluminum shielding can be obtained with polyethylene." Polyolefins that will be used in the fabrication of waste containers can absorb approximately 20 percent more cosmic rays than aluminum. Therefore, waste containers can be used to shield key areas like crew quarters.

The present invention is a multipurpose trash bag based on microporous polymer composite membranes for storing unprocessed waste and encapsulation of solid waste during the HMC process.

In order to reduce the logistical burden of storing trash during long missions, heat melt compactable trash bags are needed by NASA. It will be advantageous if the trash bags are self-decontaminating for long-term storage. Such containers can also help in radiation shielding. The present invention product, the multipurpose waste container can be used for food storage and handling, crew hygiene, solid waste treatment and storage, and waste from the biological and chemical experiments.

Waste container bags in the present invention can be extended to a variety of protection and containment markets; these include chemical and biological disposal bags/pouches, food safety and investigative sample isolation containers, fishing/hunting storage gear, and body bags.

The bags and containers can be used in military applications—especially in the Navy for both surface and undersea missions and in civilian uses in homes, factories and construction sites.

Storage containers that can be subjected to heat melt-compaction processes would find use in Navy vessels in which space is a premium. Navy ships generate high-value plastic wastes in the form of high-density polyethylene (HDPE) plastic containers and low-density polyethylene (LDPE) packaging films. The garbage sorting unit within the Navy vessels sort the recyclable food matter from the plastics, the former being discarded into the ocean to be consumed by marine life. The disposal of plastic into the ocean is dangerous for marine life such as sea turtles, which could ingest the plastic bags, mistaking them to be jellyfish. Compacting these plastic containers so that they occupy less space, will facilitate carrying these plastic bags back to shore for environmentally safe disposal or recycling.

In civilian applications, the staggering use of garbage containers and bags in domestic and industrial settings is often overlooked. World Bank reports that the amount of garbage generated in urban areas all over the world is growing at a faster rate than the rate of urbanization. It is said that each living person on earth produces 1.2 kg of garbage per day. This results in 7.4 million tons of garbage per day in the world. This staggering amount of garbage requires the use of staggering amounts of containers/bags to hold them and/or transport them to the final disposal site.

Since the introduction of the first garbage plastic bag in 1950 by the Canadians, Harry Wasylyk, Larry Hansen, and Frank Plomp, garbage bags and containers have become ubiquitous in daily life and are used extensively in homes, institutions, offices, shops, restaurants, hospitals, industries, etc. The development, use and hence the market for garbage bags has been driven by increasing health and environmental awareness among people and environmental policies implemented by various governments across the globe.

Plastic containers that are used to store radioactive material are difficult to compact, incinerate and encapsulate, even after pre-treatment such as shredding. There have been reports of the development of extruding plastic wastes into a drum under the effect of heat, to exclude unwanted air. Such developments would require the development of baggage material that can be heat-melted as provided by the present invention.

The importance of controlling oxygen, carbon dioxide and nitrogen gas atmosphere and moisture have been described by Floyd, et al., Package for perishable food and horticultural products, U.S. Pat. No. 5,908,649. The multifunctional storage bag or container can be used for controlling carbon dioxide, ethylene gas and moisture atmosphere inside the bag. For example, carbon dioxide concentration can be increased inside the bag by hermetically sealing the bag. Since the pores are sealed by polymer gel carbon dioxide will not able to diffuse out (Van Gurp, et al., Process for foil ripening of cheese. the U.S. Pat. No. 9,114,929 Aug. 25, 2015).

Alternatively, carbon dioxide gas can be removed from the bag with the use of carbon dioxide philic polymers such as polyamines infiltration inside the pores in place of PVA gel.

The storage bag can be used to store perishable items like food, vegetables, plants, and fruits from microbial attack.

The storage bag can be used to process food items like cheese and ripe fruits like apples, strawberries banana, and avocado and also protect from microbial attack.

In some embodiments, a flexible water vapor permeable, antimicrobial storage bag having an outer multifunctional layer and a porous inner support layer is provided. The outer multifunctional layer includes a hydrophilic polymer and an antimicrobial agent. The outer multifunctional layer can be a coating or a sheet with the components of the outer multifunctional layer. The hydrophilic polymer can be polyvinyl alcohol or polyvinyl pyrrolidone. The antimicrobial can be silver doped copper oxide, magnesium hydroxide, copper-doped magnesium hydroxide, silver doped magnesium hydroxide, magnesium oxide, copper doped magnesium oxide, silver doped magnesium oxide, titanium dioxide nanotubes, or silver and copper ion-exchanged titanium dioxide nanotubes. The porous inner support layer is a porous polymer sheet which can be polypropylene, nylon, polyester, polyurethane, polyimide, polytetrafluoroethylene or polyetherimide. The hydrophilic polymer behaves as an adhesive at a temperature higher than about 120 degrees C. and fills up and closes pores in the porous inner support layer. Inserting a waste material into the flexible, water vapor permeable, antimicrobial storage bag, then sealing the storage bag to encapsulate the waste material, applying vacuum and heating upto 120 degrees centigrade allows recovery of water vapor. Heating to higher than 120 degrees centigrade configures the flexible, water vapor permeable, antimicrobial storage bag to a substantially water vapor impermeable, antimicrobial product. The flexible, water vapor permeable, antimicrobial storage bag has an opening to receive a waste material. The substantially water vapor impermeable, antimicrobial product is pressure compressible into a sealed disc. The compression of the storage bag containing waste material does not cause disintegration of the storage bag, i.e., the storage bag maintains its integrity when heated to higher than 120 degrees centigrade under vacuum and undergoing compression. The flexible, water vapor permeable, the antimicrobial storage bag is impermeable to liquid water at room temperature and at temperatures of upto 120 degrees centigrade and higher.

In some embodiments, methods of using a storage bag to recover water vapor from waste material, while providing water vapor impermeability and antimicrobial property useful for storage of waste material within the storage bag are provided. In some methods, a flexible water vapor permeable antimicrobial storage bag is prepared. Then a waste material is inserted into the storage bag through an opening in the storage bag. Then the opening in the storage bag is sealed, and vacuum is applied along with heating upto 120 degrees centigrade to recover water vapor from the contents of the storage bag. Then the heating temperature is raised to higher than 120 degrees centigrade to create a substantially water vapor impermeable antimicrobial heat treated product. The heating extracts out water vapor and makes the storage bag substantially water impermeable. Preparation of storage bag includes coating an outer multifunctional layer onto a porous inner support layer to obtain a multilayer sheet. The outer multifunctional layer includes a hydrophilic polymer and an antimicrobial agent. The hydrophilic polymer can be polyvinyl alcohol or polyvinyl pyrrolidone. The antimicrobial can be silver doped copper oxide, magnesium hydroxide, copper-doped magnesium hydroxide, silver doped magnesium hydroxide, magnesium oxide, copper doped magnesium oxide, silver doped magnesium oxide, titanium dioxide nanotubes, or silver and copper ion exchanged titanium dioxide nanotubes. The porous inner support layer includes a porous polymer sheet which can be polypropylene, nylon, polyester, polyurethane, polyimide, polytetrafluoroethylene, or polyetherimide. The hydrophilic polymer behaves as an adhesive at a temperature higher than about 120 degrees C. and fills up and closes pores in the porous inner support layer. The water vapor permeable, antimicrobial storage bag is flexible and includes an open section to receive waste material. Further, the substantially water vapor impermeable antimicrobial heat treated product can be compressed to obtain a compressed, water impermeable, antimicrobial product which encapsulates and completely covers the waste material.

In some embodiments, the storage bag is prepared by laminating a porous inner support layer with an outer multifunctional sheet to obtain a multilayer sheet.

The storage bag can be used to store trash generated in submarines, Antarctica missions, space, long duration flights, restaurants which are limited in space to store trash bags.

It will be readily understood by the skilled artisan that numerous alterations may be made to the examples and instructions given herein. These and other objects and features of present invention will be made apparent from the following examples. The following examples as described are not intended to be construed as limiting the scope of the present invention.

EXAMPLES

Example 1. Synthesis of Copper (II) Oxide and Silver-Doped Copper (II) Oxide (Ag—CuO) Nanoparticles To synthesize the nanoparticles, 0.76 g of Polyoxyethylene (20) sorbitan monooleate (also known as polysorbate 80 or Tween 80) was dissolved in 100 mL of water by heating the solution to 80 degree C. while stirring. 100 mL of 0.4 M copper acetate solution was then added to the Tween 80 solution and stirred for 30 minutes. Separately, 500 mL of 1M NaOH solution was formed. After the Tween 80/copper acetate solution had stirred for 30 minutes, the NaOH solution was added dropwise. The temperature of the solution remained at 70-80 degree C. with constant stirring during this process. Once all of the NaOH had been added, the solution was left to react over heat for two hours. After two hours had passed, the solution was cooled to room temperature. The solution was then centrifuged, and the supernatant was poured off. The nanoparticles were then washed with distilled water and centrifuged again. These particles were left to dry overnight. The nanoparticles were then dried in the oven at 110 degree C. for one hour. Once the nanoparticles had cooled to room temperature, an XRD analysis was run. The XRD analysis determined that the product was primarily copper (II) oxide.

Synthesis of Silver Doped-Copper Oxide (Ag—CuO)

Figure 2:
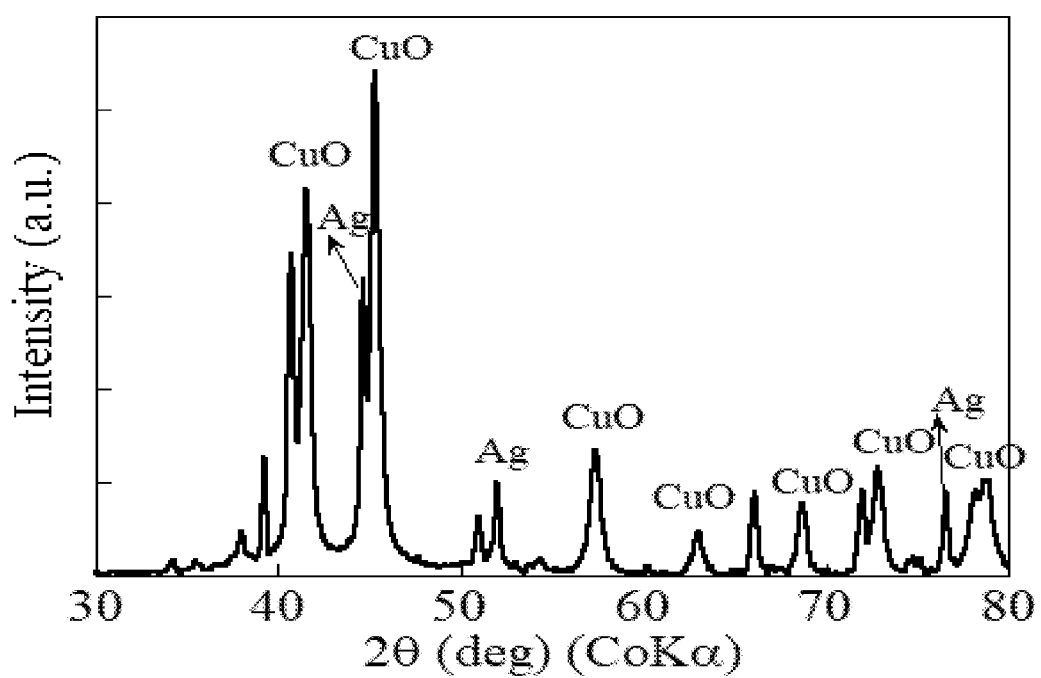
FIG. 2 provides powder X-ray diffraction pattern of silver doped copper oxide. Diffraction peaks corresponding to copper oxide (CuO) and silver metal are marked.

Silver doped CuO powders were prepared by precipitation method. Sodium hydroxide solution was added to a mixer containing copper acetate and silver nitrate. The Ag—CuO particles formed were separated by centrifugation, washed with water and dried at 110° C. The powder XRD pattern of Ag—CuO powder was measured using Rigaku Miniflex® X-ray diffractometer and is provided in FIG. 2. The surface area of the Ag—CuO powder was measured using Coulter SA 3100 surface area analyzer. The surface area was about 17 $m^2/g$.

Example 2. Preparation of CuO/PVP Polymer Gel-Filled Microporous Composite Membranes To prepare the solution for the gel, 20 g of polyvinylpyrrolidone (PVP) was dissolved in 500 mL of distilled water. The PVP was added very slowly as the water was heated to around 70-80 degrees C. The solution was then cooled to room temperature. Once the solution had cooled, 15 g of ammonia persulfate was added to the PVP solution.

The microporous polymer film has a hydrophobic surface and does not allow for the water-based solution to fill the pores of the film. In order to alter the surface to become hydrophilic, the film was oxidized by placing the samples into an 8"×8" glass dish filled with 200 mL of water and 2 g of potassium permanganate. This glass dish was then placed in a microwave in 10-second intervals. After each 10 second interval, the film was rinsed with distilled water to see if it would wet. The samples stopped repelling the water after twenty 10-second intervals.

Oxidized samples were used to infiltrate the PVP solution into the pores of the microporous film. The samples were left to soak in the solution overnight to ensure that the pores were filled. Once the samples were removed from the solution, they were hung on a rack in order to form a thin coating of gel. The samples were heated in an oven at 110 degrees C. for 5 minutes. This resulted in the formation of a visible film of gel on the surface of the samples.

Example 3. Synthesis of PVP Gel with Nanoparticles

Copper (II) oxide nanoparticles were introduced into the PVP solution by adding 1 percent of the particles to 50 mL of the PVP gel solution. This mixture was stirred until the nanoparticles dissolved in the solution and caused it to turn blue. The solution was then heated at 80 degrees C. for over an hour; however, the solution did not gel.

Example 4. Mixing of CuO Nanoparticles into Preformed Gel

A gel was formed by heating 25 mL of PVP solution to approximately 80 degree C. Once the gel had formed, 0.25 g of CuO nanoparticles were added. This mixture was stirred at room temperature as the nanoparticles were dissolved. The resulting gel had turned blue. Due to the copper (II) oxide nanoparticles dissolving in the ammonia persulfate catalyst, potassium persulfate was alternatively used in the solution. This solution was formed by first dissolving 4 g of PVP into 100 mL of water at 80 degrees C. Once the PVP had dissolved, 3 g of potassium persulfate was added to the solution at room temperature. After the potassium persulfate had dissolved into the solution, 1 g of copper (II) oxide nanoparticles was mixed into the solution. The nanoparticles dispersed into the solution causing it to appear black in color. The mixture was then heated at approximately 80 degrees C. in order to attempt to form a gel. The addition of heat to this mixture caused the nanoparticles to dissolve into the solution turning it blue. This solution was heated for over 30 minutes; however, a gel did not fully form. The bottom of the solution appeared to form a small amount of a gel-like substance. However, the solution did not gel properly in order to be useful. Therefore, PVP gel should be washed completely with water to remove excess unreacted ammonium persulfate or potassium persulfate before adding copper (II) oxide nanoparticles into PVP gel.

Example 5. Forming Gel Using Polyvinyl Alcohol (PVA) and Sodium Tetraborate

Due to the inability of the PVP and ammonia persulfate solution to properly form a gel when mixed with copper (II) oxide nanoparticles, the polymer solution was switched to PVA. The PVA polymer was able to form a gel quickly without applying heat and could form a gel when nanoparticles were dispersed within it.

PVA was used as the polymer for the gel by dissolving 4 g of PVA into 50 mL of distilled water at 80 degrees C. This solution was then cooled to room temperature. Pieces of the oxidized microporous film were then placed into this solution to soak overnight. A sodium tetraborate solution was then formed by dissolving 4 g of the solid in 100 mL of water. The PVA soaked samples were then dipped into the sodium tetraborate solution. The resulting sample had a uniform layer of gel formed onto its surface. These samples were then left to air dry so that a hardened film layer remained in the sample.

Example 6. Forming Gel Using PVA, CuO Nanoparticles, and Sodium Tetraborate

An 8 percent solution of PVA was made by dissolving 20 g of PVA into 250 mL of distilled water at 80 degrees C. The solution was then cooled to room temperature, and 2.5 g of CuO nanoparticles were added to the solution. Oxidized pieces of single layer microporous-1 film were then placed into this solution to soak overnight. The PVA soaked samples were then dipped into the sodium tetraborate solution. The resulting sample had a uniform layer of gel formed on its surface that was densely black in color in some areas. These samples were then left to air dry so that a hardened film layer remained in the sample.

Example 7. Spraying of CuO Nanoparticles onto PVA Gel Coated Single Layer Microporous-1 Sheet Samples of single layer microporous-1 sheet were treated using the procedure above to form a PVA gel coating on the film. A 5 wt percent copper (II) oxide solution in water was formed in order to spray the samples with. The samples were sprayed with this solution on both sides using a liquid sprayer. The coated samples were then placed in an oven at 110 degrees C. for 5 minutes. The resulting material was black in color due to the surface being coated with a layer of CuO particles.

Example 8. Effect of Time on Gel Infiltration

Oxidized samples of Single-layer microporous-1 and Single layer microporous-2 polymer sheet were used in order to determine the effect of polymer soaking time on the weight increase of the film. The samples were soaked in solutions of PVA or PVP for 2 hours, 3 hours, or 4 hours. The results of this experiment are shown in Table 1.

TABLE 1

Relationship between time and weight increase

| Polymer Used | Time Soaking (hours) | % Weight Increase | Standard Deviation |
|---|---|---|---|
| PVA | 2 | 3.00 | 1.09 |
|  | 3 | 3.84 | 2.34 |
|  | 4 | 3.49 | 0.34 |
| PVP | 2 | 2.21 | 0.59 |
|  | 3 | 2.95 | 0.96 |
|  | 4 | 2.98 | 0.25 |

After two hours, there was a significant weight increase in the Single layer microporous-1 sheet due to the polymer solution. Between three and four hours the polymer did not cause a significant weight increase. Therefore, we down-selected the time of reaction to be about 3 hours.

Example 9. Effect of Oxidation Time on Hydrophilic Treatment of Single-Layer Microporous-1 Film Pieces of Single-layer microporous-1 film were placed into 600 mL of 1 percent potassium permanganate. Every 10 minutes the contact angles were taken after the samples were rinsed with water and dried.

TABLE 2

Relationship between contact angle of Single-layer microporous-1 film and oxidation time

| Time Elapsed (min) | Contact Angle Average |
|---|---|
| 0 | 111.46 ± 2.37 |
| 10 | 86.94 ± 4.31 |
| 20 | 81.16 ± 4.14 |
| 30 | 75.42 ± 2.57 |
| 40 | 73.68 ± 2.04 |
| 50 | 73.30 ± 2.23 |
| 60 | 71.58 ± 2.26 |

The results from Table 2 show that treatment with potassium permanganate effectively reduces the water contact angle of the Single layer microporous-1 polymer sheet and allows for wetting of the surface with water. This wetting allows for the surface to become hydrophilic and allow a water-based gel into the pores of the film. Therefore, we have down-selected the time of reaction to be about 20 min.

Thickness of Microporous Films

The thickness of the Single layer microporous-1 and Single layer microporous-2 polymer sheets were measured using a digital micrometer.

TABLE 3

Thickness of microporous polymer sheets (gsm = gram per square meter)

| Material Type | Thickness (mm) |
|---|---|
| Single layer microporous-1 polymer sheet | 0.036 |
| Single layer microporous-2 polymer sheet | 0.042 |
| Commercial Trash Bag | 0.020 |
| Multilayer microporous polymer sheet-60 gsm | 0.25 |
| Multilayer microporous sheet-120 gsm | 0.50 |

From this data, it was determined that the materials that are being used in this experiment are much thinner than the bags currently used for HMC processing.

Effect of Heat on Single Layer Microporous-1 Sheet

Single layer microporous-1 polymer sheets were treated with a PVA and CuO nanoparticle solution as described above in order to form a gel on the material. These samples were then heated at various temperatures for 10 minutes each in order to determine the shrinkage of the material at each temperature.

TABLE 4

Shrinkage of Single layer microporous-1 film due to heat

| Temperature (° C.) | Average % Shrinkage of Area |
|---|---|
| Room Temperature (~25) | 0 |
| 70 | 0 |
| 100 | 2.94 ± 1.31 |
| 110 | 3.40 ± 0.48 |
| 120 | 2.18 ± 0.79 |
| 130 | 3.24 ± 0.75 |
| 140 | 4.62 ± 1.46 |
| 150 | 9.29 ± 0.82 |

During this testing, the material appeared to mostly shrink in one direction, causing the material to form a more rectangular shape. As the temperature increased, so did the rate of shrinking. At a temperature of 150 degrees C., the material shrank the most. However, over extended periods of time the material stopped shrinking, and over 12 hours the material began to melt.

Testing Using Hydrophilic Polymer Treated Single Layer Microporous-1 Polymer Sheets In order to determine the water vapor transport rate of the Single layer microporous-1 polymer sheets, the oven was first equilibrated. The oven was stabilized at a temperature of 35 degrees Centigrade and a relative humidity of less than 16 percent. The humidity was maintained less than 16 percent. Vials were filled with 15 mL of distilled water and capped. The vial assembly consisted of a membrane and cored septa sealed onto a glass vial using an open-top cap. Once the oven had stabilized, the vials were then placed into the oven. The vials remained in the oven for five days.

The gel coated polymer sheets were formed by first placing oxidized samples of Single-layer microporous-1 polymer sheets into a 4 percent PVP polymer solution. These samples were then left in to soak in the solution overnight. In the morning, the samples were then removed from the solution and heated at 80 degrees C. for 10 minutes. One of the samples was then soaked in a 0.1 M Copper acetate solution overnight in order to form the PVP coated samples with copper ions. The results of this experiment can be found in Table 5.

TABLE 5

Water Vapor Transport Rate Data of Single layer

| Treatment | WVTR (g/m$^2$/day) | Average % Lost Per Day |
|---|---|---|
| Uncoated | 1130.095 | 0.711 |
| PVP Coated | 3037.119 | 1.969 |
| PVP Coated w/ Cu ions | 2961.128 | 1.934 |

Both of the gel coated samples nearly tripled the water vapor transport rate of that of the uncoated sample.

Testing Using Oxidized Single Layer Microporous-1 Polymer Sheets and Single Layer Microporous-2 Polymer Sheets To test oxidized samples, the procedure that was used for the other Single layer microporous-1 polymer sheet was applied here as well. These polymer sheets were treated using the oxidizing procedure as described above. The results of this experiment can be found in Table 6.

TABLE 6

Water Vapor Transport Rate Data of Oxidized Films

| Film Type | Treatment | WVTR (g/m²/day) |
|---|---|---|
| Single layer microporous-2 polymer sheet | Untreated | 2838.801 |
| Single layer microporous-2 polymer sheet | Oxidized | 2868.288 |
| Single layer microporous-1 polymer sheet | Oxidized | 1156.212 |

The results of this experiment prove that the oxidation process does not have a significant effect on the water vapor transport rate of the film.

Testing of Gel Treated Single layer microporous-1 polymer sheets

Single layer microporous-1 polymer sheets were treated with PVA and PVP gels by first oxidizing pieces of the film in 1 percent potassium permanganate solution for 1 hour. The samples were placed into either an 8 percent PVA (31,000-50,000 MW), 4 percent PVA (140,000-180,000 MW), 8 percent PVA (31,000-50,000 MW) with 1 percent CuO nanoparticles, or 4 percent PVP solution to soak overnight. In the morning, the samples were rinsed with excess polymer solution by dipping them in distilled water. The PVA samples were then placed in a 4 percent sodium tetraborate solution and dried. The PVP samples were heated at 110 degrees C. for 5 minutes. Once all of the samples had been fully treated, the procedure used above to perform a water vapor permeation test was followed. The results of this experiment can be found in Table 7.

TABLE 7

Water Vapor Transport Rate Data Gel Treated Single layer microporous-1

| Treatment | WVTR (g/m²/day) | | |
|---|---|---|---|
| | 35° C. | 50° C. | 70° C. |
| PVA (31,000-50,000 MW) | 970.53 | 1678.209 | 10172.37 |
| PVA (140,000-180,000 MW) | 768.34 | 1937.691 | 6373.15 |
| CuO and PVA (31,000-50,000 MW) | 1233.38 | 2104.5 | 8275.79 |
| PVP | 798.67 | 3014.37 | 6710.81 |

The results of this experiment show that a higher molecular weight polymer decreased the water vapor transport rate of the film significantly. This experiment also proves that an increase in temperature does affect the water vapor transport rate to increase greatly as more water vapor is produced.

Testing of Gel Treated Single Layer Microporous-2 Polymer Sheet

Single layer microporous-2 polymer sheet has been addressed with polymer gels using the same procedure for the Single layer microporous-1 films. After treatment, WVTR testing was conducted.

TABLE 8

Water Vapor Transport Rate Data Gel Treated Single layer microporous-2

| Treatment | WVTR (g/m²/day) | | |
|---|---|---|---|
| | 35° C. | 50° C. | 70° C. |
| PVA (31,000-50,000 MW) | 2577.97 | 6284.18 | 50376.59 |
| PVA (140,000-180,000 MW) | 2173.58 | 5439.01 | 20047.52 |
| CuO & PVA (31,000-50,000 MW) | 2466.76 | 6965.58 | 29115.91 |
| PVP | 2658.85 | 6221.50 | 29055.25 |

The results of this experiment show that the Single layer microporous-2 material has a much higher water vapor transport rate than the Single layer microporous-1 film.

Testing of PVA Treated Single Layer Microporous-1 at 50 Degrees C. and Under Vacuum Samples were prepared for this experiment by first oxidizing the Single layer microporous-1 film by placing it into a 1 percent potassium permanganate solution for an hour. The samples were then placed into an 8 percent PVA (31,000-50,000 MW) solution to soak overnight. Next day the samples were removed and rinsed with distilled water to remove any excess polymer from the surface of the material. The samples were then dipped into a 4 percent sodium tetraborate solution to form a gel. The samples were then dried in order to begin sealing them. To form a bag using this material, hot glue was applied to the edges of the bag. Duct tape was then added to the hot glue seal in order to ensure that the bag would remain shut during testing. Previous attempts at performing this experiment resulted in the bag opening during vacuum application, so extra precautions were taken to fully seal the bag. The formed bag was then placed into a glass desiccator that was in an oil bath. The inside of the glass desiccator was heated to 50 degrees C., and a vacuum pressure of 14.25 psi was applied. The results of this experiment can be found in Table 9.

TABLE 9

Water Vapor Transport Rate Data of PVA at 50 degrees C and Under Vacuum

| Treatment | WVTR (g/m²/day) |
|---|---|
| PVA (31,000-50,000 MW) | 5148.94 |

From this data, it can be determined that under vacuum the material has a much higher water vapor transport rate.

Effect of Heat Treatment on the Water Vapor Permeation Rate of PVA/CuO Coated Samples Treated (PVA/CuO) Multilayer layer microporous Y120 sheets were heated to various temperatures for 10 min to investigate the effect on the material's water vapor permeation rate. The ASTM E 96-95 (Standard Test Methods for Vapor Transmission of Materials) procedure was followed. 20 mL glass vials, with open-top caps and Teflon-lined septa (14-mm hole), were used. The heat-treated samples were placed inside the cap with the cored septa placed behind the membrane to provide an airtight seal. The vials were filled with 10 mL of distilled water and placed in an airtight oven at 35 degree C. The weight of the vials was measured after 24 h to calculate the total weight loss of water and the corresponding permeation rate.

The water vapor permeation rate significantly decreased for samples heated to 120 degree C. and 150 degree C.

indicating the sealing of pores in the polymer membrane. There was no significant difference in the permeation rate of samples heated to 90 degrees C. and below. The infiltrate multilayer layer microporous Y120 is composed of a different material on each side. Therefore, the permeation rate was measured in each direction with one side being texturized and the other being relatively smooth. T-OUT corresponds to the texturized side facing away from the vial interior while T-IN corresponds to the texturized side facing the vial interior. The permeation rate was higher when the texturized side was facing the interior of the vial. The above procedure was repeated using an oven temperature of 70 degrees C. and measuring the weight of the vials every 2 hours.

TABLE 10

Water Vapor Permeation Rates of PVA/CuO Treated Infiltrate Multilayer layer microporous Y120 heated to various temperatures at 35 degree C. according to ASTM E-96 standard method

| Temperature (° C.) | Membrane Direction | Water Vapor Permeation Rate (g/(m$^2$day) |
|---|---|---|
| N/A | T-OUT | 4140 ± 494 |
| 60 | | 4680 ± 428 |
| 90 | | 4530 ± 539 |
| 120 | | 1260 ± 740 |
| 150 | | 292 ± 101 |
| N/A | T-IN | 4910 ± 396 |
| 60 | | 4690 ± 555 |
| 90 | | 4740 ± 441 |
| 120 | | 2540 ± 1320 |
| 150 | | 983 ± 169 |

TABLE 11

Water Vapor Permeation Rates of PVA/CuO Treated Infiltrate Multilayer layer microporous Y120 heated to various temperatures measured at 70 degree C. according to ASTM E-96 standard method

| Temperature (° C.) | Membrane Direction | Water Vapor Permeation Rate (g/(m$^2$day) |
|---|---|---|
| N/A | T-OUT | 19500 ± 5060 |
| 60 | | 16300 ± 2910 |
| 90 | | 16200 ± 4420 |
| 120 | | 3750 ± 868 |
| 150 | | 1290 ± 183 |
| N/A | T-IN | 15860 ± 3520 |
| 60 | | 18200 ± 5050 |
| 90 | | 15100 ± 3280 |
| 120 | | 7290 ± 2690 |
| 150 | | 3230 ± 1360 |

The WVTR data provided in Table 10 and 11 clearly demonstrate that pores in the PVA/CuO coated sheets were sealed when heated above 120 degrees C. When the microporous material was heat treated above 120-degree C. for 10 minutes, the WVTR value was decreased by about at least 4 times lower than for untreated multilayer material. The decrease in WVTR value can be as high as 16 times in some embodiments. This is exactly what is required for storing the HMC processed disks for a long duration. The HMC processed contaminants will be sealed or encapsulated by the multifunctional waste disposal bag when heated above 120 degrees Centigrade.

Design and Fabrication of Composite Membrane Trash Bag

Multilayer layer microporous Y120 is a two-layer polymer material supplied by Pragma Engineered Fabrics composed of a vapor permeable and liquid resistant microporous polyethylene film that is laminated with spun bound polypropylene for improved durability and feel.

Figure 3:
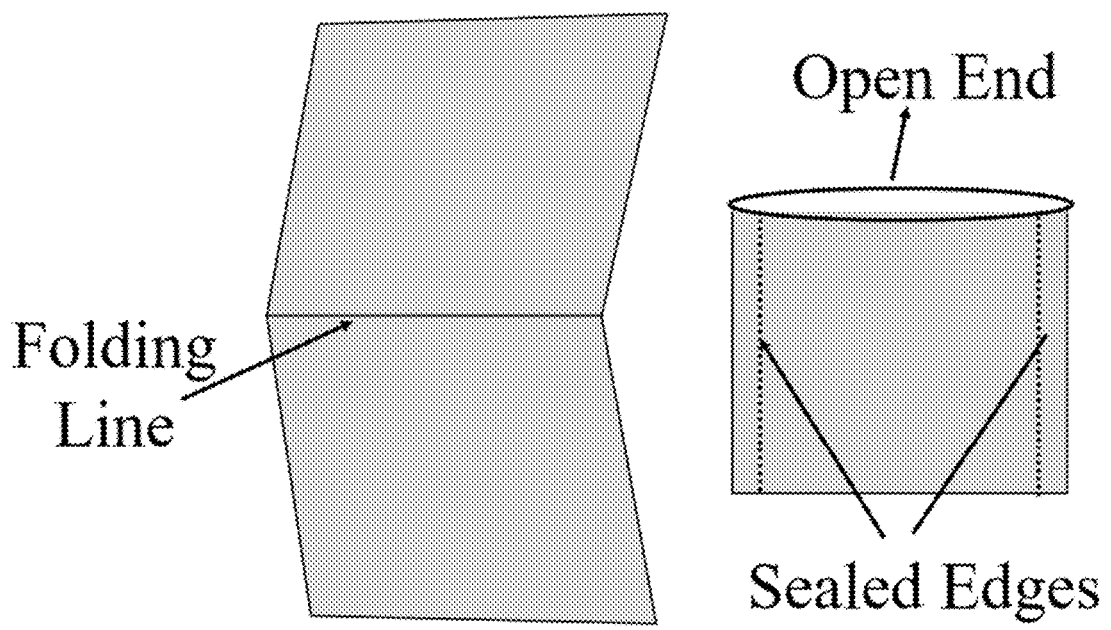
FIG. 3 provides a picture of Multilayer layer microporous Y120 before and after heat sealing (right).

Bags of Multilayer layer microporous Y120 were prepared by cutting 6" by 12" sheets of the material from a 60" roll. The sheets were then folded in half to form a square with the polyethylene side on the exterior of the bag. An image of the multifunctional bag is provided in FIG. 3. The folded sheets were sealed (0.4 s; double-wire) along the 12" folded edge using the heat sealer. The heat sealer works by pressing together two sheets of thermoplastic material along a heated seam line. The sheets become bonded along the seam line as the polymers are simultaneously compressed and melted together. The sheets should remain pressed together for 10 s upon cessation of heating to allow the polymers to solidify under pressure to form a durable bond.

The bags were then chemically treated to activate the surfaces for the infiltration of hydrophilic polymeric gel. The bags were soaked in an aqueous solution of potassium permanganate (1 percent by wt.) for 30 min. The bags were then thoroughly rinsed with water to remove residual potassium permanganate. The oxidized bags were soaked for 2-18 h in an aqueous solution of polyvinyl alcohol (31,000-50,000 MW) (4 percent by wt.) and copper (II) oxide (1 percent by wt.). The bags were rinsed with distilled water to remove excess PVA on the bag surface. The rinsed bags were soaked for 1-2 h in an aqueous solution of sodium tetraborate decahydrate (4 percent by wt.) and CuO (2 percent by wt.). Sodium tetraborate crosslinks with PVA present on the bags resulting in the formation of a highly cross-linked PVA polymer inside the pores of the polymeric membrane. The CuO dispersed in the solution becomes trapped in the rapidly forming PVA network which will impart anti-microbial properties onto the bag. The bags were air dried to give PVA/CuO infiltrated Multilayer layer microporous Y120 bags (Infiltrated Y120 bags).

Heat Melt Compaction Testing Using Simulated Trash
Preparation of Trash Simulant Mixture A simulant for trash produced on the ISS was prepared for testing of the treated trash bags. The trash simulant contains food and non-food related items similar in composition to the trash produced on the ISS. The non-food related items were cut into pieces no larger than 1" by 1" and thoroughly mixed in a 2.5-gallon Polyethylene bag. The food items were thoroughly mixed in a separate Polyethylene bag. The mixture of non-food items was then added to the bag containing food items, and the contents were thoroughly mixed for 20 min. The simulants were mixed by vigorously pressing and shaking the items together by hand until the food items were evenly dispersed.

Testing of Water Recovery

PVA/CuO infiltrated Multilayer layer microporous Y120 bags (3" by 3" with an outer membrane total surface area of 42.9 cm$^2$) were filled with 15.0 g of trash simulant, sealed with a liquid sealant, and placed inside a stainless steel container. The container was connected to a vacuum pump through a cold trap. The trash bag was heated at 90 degrees C., and the vacuum pressure was held between 10-20 mbar.

The weight change of the bag was calculated for every 30 min time interval (Table 15). The estimated water content of the trash simulant was 31.43 percent (Estimated percent water in trash simulant=100×(Estimated water weight of trash simulant)/(Total weight of trash simulant)=100× (159.74/508.25)=31.43 percent). Based on the estimated water content in each bag, the percent water removed from each bag was calculated to be above 95 percent (Table 12).

TABLE 12

Water vapor permeation rate across infiltrated Multilayer layer microporous Y120 bags

| Weight of Trash Simulant (g) | Weight Change per Time Interval (g) | | | | | | | | Estimated Water Content of Simulant (g) | Percent Water Removed (%) |
|---|---|---|---|---|---|---|---|---|---|---|
| | 0-30 min | 30-60 min | 60-90 min | 90-120 min | 120-150 min | 150-180 min | 180-210 min | Total 0-210 min | | |
| 14.97 | 1.43 | 1.15 | 1.00 | 0.58 | 0.22 | 0.10 | 0.00 | 4.47 | 4.71 | 95.10 |
| 14.97 | 1.55 | 1.35 | 0.78 | 0.57 | 0.23 | 0.02 | 0.08 | 4.58 | 4.70 | 97.26 |

This test results clearly demonstrated the objective of removing water from trash without the need for melting the trash bag.

PVA/CuO infiltrated Multilayer layer microporous Y120 bags (6"×6") were filled with trash simulant (50.0 g). The bags were sealed with a liquid sealant (3M SF-100) by applying a thick bead of the adhesive along the inside edge of the open side which was then clamped shut until dried. This method of sealing of bag proved to be the better than heat sealing after loading with trash. A single trash-filled bag was then placed in a vacuum chamber. The vacuum chamber was sealed, and its metal bottom was placed directly on a hot plate and heated to maintain an internal chamber temperature of 90 degrees C. The pressure inside the chamber was then reduced to 10-20 mbar by an external vacuum pump. After 1 h, the bag was removed from the vacuum chamber.

The melting and compaction testing chamber were designed to simulate the unit of the Heat Melt Compactor that melts and compacts trash bags after water removal and collection. The bag is positioned by hand inside the testing chamber so that one the 6" diameter face was in flush with the surface of the bottom aluminum disc. An aluminum disc was then lowered into the chamber until it's resting on top of the trash bag. The testing chamber was then heated to 180 degrees C. for 1 h. The testing chamber was removed and placed directly below the ram.

Figure 4:
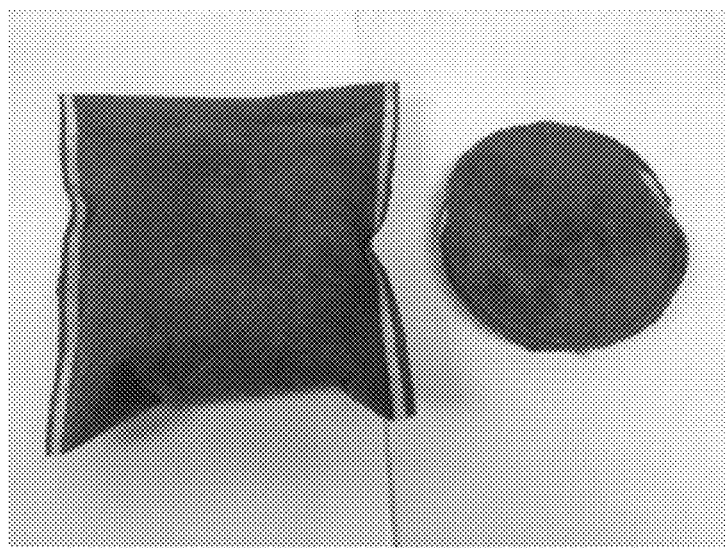
FIG. 4 provides a treated (PVA/CuO) Multilayer layer microporous polymer bag containing trash simulant (left) and after heat-melt-compaction (right).

The ram was lowered into the testing chamber until the upper aluminum disc was applying a pressure of 80 psi. The trash bag was compacted as it was pressed by the force of the ram between the two aluminum discs. The pressure was maintained for 10 min as the bag cooled and solidified to form a circular disc as provided in FIG. 4. The ram was then retracted, and the base of the testing chamber was unscrewed from the cylinder to obtain the melt-compacted trash bag.

Comparison of Infiltrated Multilayer Layer Microporous Y120 and Polyethylene Bags A quart-sized polyethylene bag was filled with trash simulant (50.0 g). The bag was then placed in a vacuum oven at 90 degrees C. The pressure inside the oven was reduced to 10-20 mbar. The bag was kept in the oven for 1 h in an attempt to remove water from the trash simulant. However, it was determined that water was not able to permeate the Polyethylene bag at these conditions as there was not a significant change in the weight of the bag. The bag was then placed in the testing cylinder, and an aluminum disc was inserted above it. The testing cylinder was heated to 150 degree C. for 2 h. The chamber was then removed from the oven and placed below a ram. The ram was lowered, and a pressure of 80 psi was applied to disc at the top of the testing cylinder for 10 min. The testing cylinder was allowed to cool to ambient temperature, and the compressed bag was removed.

The density of the compressed Polyethylene bag and Multilayer layer microporous Y120 containing trash simulant was calculated to be 99 and 95 kg/m3, respectively.

Evaluation of Antimicrobial Efficiency of Heat Melt Processed Trash

Antimicrobial testing was performed on the CuO/PVA loaded membranes along with HMC processed disks, as well as a control material. Approximately 10 g of each test specimen was placed in a 50 mL centrifuge tube along with 100 µL of bacteria (*E. coli*). A pellet was placed in each tube, and they were put in a shaker incubator overnight. Afterwards, the 1004, of bacteria was taken from each tube and plated in a petri dish. These were then incubated upside down overnight.

Figure 5:
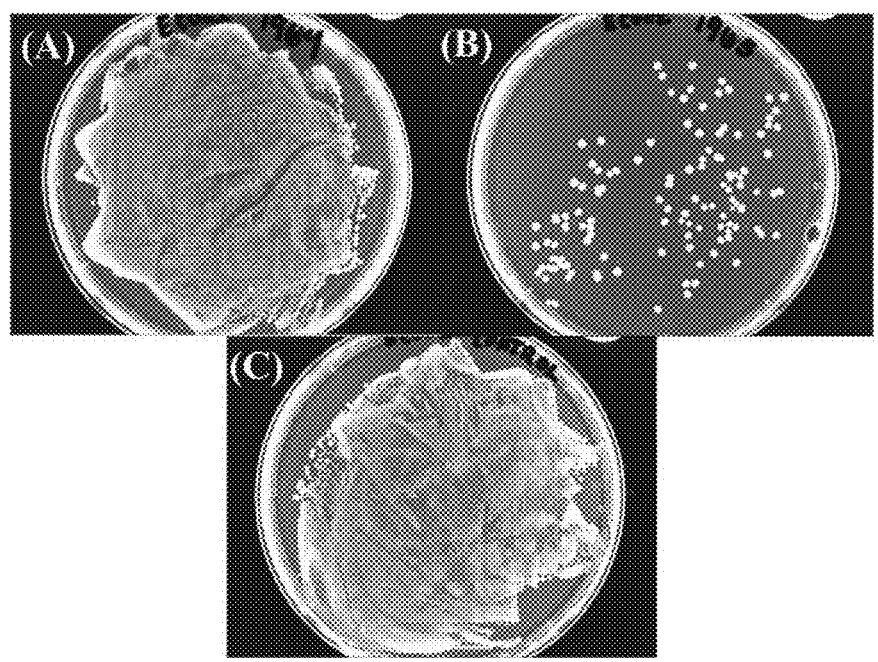
FIG. 5 shows images of microbial growth on plated samples: (A) CuO treated bag, (B) Silver doped CuO treated bag, and (C) control.

As shown in FIG. 5, there was the substantial growth of *E. Coli* on the CuO treated bag and the control sample. The dual treatment of Silver-doped CuO showed significantly reduced numbers of colonies present after incubation indicating the antimicrobial property of the silver-doped CuO coated multifunctional trash bags.

Figure 6:
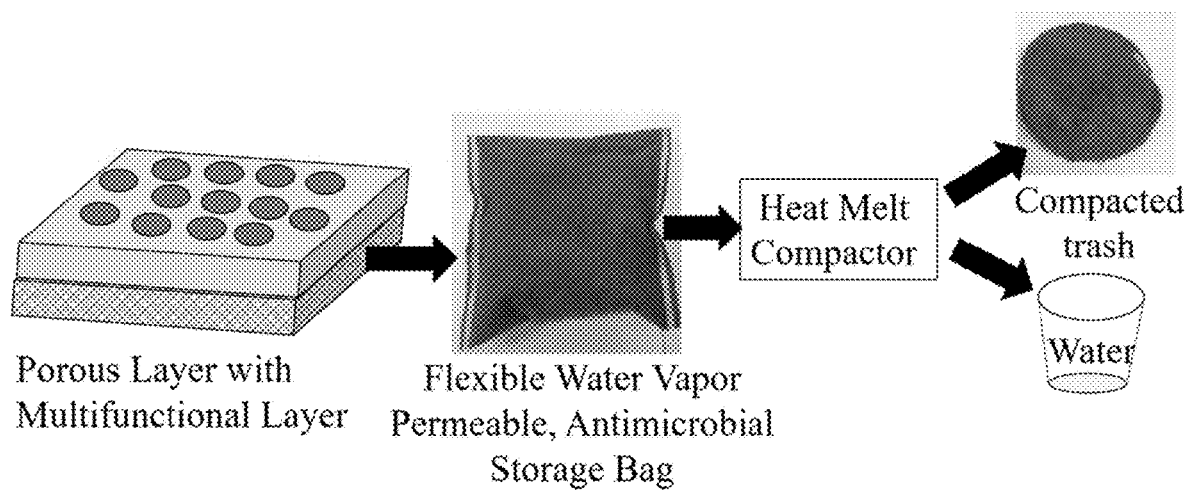
FIG. 6 provides a schematic representation of application of a multifunctional trash bag or storage container.

The results clearly demonstrated that the HMC compacted samples using the present invention product, a multifunctional trash bag can be stored for long durations without microbial infestation. The application of multifunctional trash bag or waste storage container is schematically described in FIG. 6.

It was decided to use polymers such as PEBAX® and Arnitel®, which are hydrophilic, breathable and high-temperature stable (>200 degree C.). Pebax® is a thermoplastic elastomers consist of polyamide and polyether backbone blocks. Arnitel is a thermoplastic copolyester elastomers. These materials have high WVTR values as provided in Table 13. The extruded breathable polymer sheets offer water vapor permeability while remaining impermeable to liquids. Because these polymer sheets are non-porous, they are used as microbial barrier protection. Pebax® thermoplastic elastomers consist of polyamide and polyether backbone blocks available from Arkema. Arnitel® is a high-performance ThermoPlastic Copolyester (TPC) available from DSM.

TABLE 13

Water Vapor Transport Rate of breathable polymer sheets

| Material | Thickness (Micron) | WVTR (g/m²/day) |
|---|---|---|
| Arnitel | 40 | 1886 |
| Pebax | 10 | 2989 |

Extrusion of Arnitel Breathable Membranes

Arnitel VT 3401 resin (RE1202301, batch #105041478 32D durometer, 414 degreeF (212 degree C.) melting point) was purchased from DSM. The resin was dried at 150 degree F. (66 degree C.) overnight before extrusion. The Arnitel pellets were put into an extruder hopper. A rotating screw inside the extruder barrel provided mechanical mixing of the pellets. Heat and mechanical energy gradually melted the Arnitel pellets. The molten polymer was conveyed or "pumped" by a rotating screw to a flat die (24" length) with a slit opening. Molten polymer exiting the extruder die was picked up by rotating rollers, solidified, and pulled to the winder. Extruder barrel temperatures at 500-510 degree F. (269-266 degree C.), Die temperatures at 465 degree F. (241 degree C.) with 2 mil film, with extrusion rate of about 11 ft./min. The extruded polymer sheets were collected on paper support.

Lamination of Arnitel Membranes onto Nylon Fabric

Nylon fabric was procured from Testfabrics, Inc. West Pittston. Nylon fabrics have been coated with an EVA based heat melt Strongbond 8115. Molten Arnitel VT 3401 polymer from the extruder was conveyed or "pumped" by a rotating screw to a flat die (24" length) with a slit opening. Molten polymer exiting the extruder die was picked up by rotating rollers, and combined with the nylon fabric fed from another roller. The molten Arnitel polymer sheet was solidified on to nylon fabric and pulled to the winder. This resulted in the lamination of Arnitel sheet only nylon fabrics.

The thickness of pristine nylon fabric was 0.168 mm, of nylon with a heat melt layer was 0.205 mm, and of Nylon with an Arnitel layer was 0.227 mm. This corresponds to an Arnitel thickness of 23 microns.

WVTR Measurements

The extruded breathable polymer sheets provide water vapor permeability while remaining impermeable to liquids. Because these polymer sheets are non-porous, they are used as microbial barrier protection. Pebax® thermoplastic elastomers consist of polyamide and polyether backbone blocks available from Arkema. Arnitel® is a high-performance ThermoPlastic Copolyester (TPC) available from DSM.

WVTR measurement on Arnitel laminated Nylon (Arnitel/Nylon) fabric was conducted at 35° C. and 70° C. to determine the effect of temperature on the WVTR of as-prepared Arnitel/Nylon fabric (Table 14). As expected, the WVTR increased at a higher temperature. However, the WVTR values are about 11 times lower for Arnitel/Nylon fabric as compared to the microporous membrane (1728 vs. 19500 g/m2/day).

TABLE 14

Water Vapor Transport Rate of breathable polymer sheets

| Material | Temperature (° C.) | WVTR (g/m$^2$/day) |
|---|---|---|
| Arnitel/Nylon | 35 | 472 |
| Arnitel/Nylon | 70 | 1728 |

Arnitel/Nylon polymer composite sheets were heated to various temperatures for 10 min to investigate the effect of treatment temperature on the material's water vapor permeation rate. The WVTR data of Arnitel/Nylon composite fabric heated to various temperatures are provided in Table 15.

TABLE 15

Water Vapor Permeation Rates of Arnitel/Nylon Fabric heated to various temperatures

| Membrane Treatment Temperature (° C.) | Water Vapor Permeation Rate (g/(m$^2$day) 35° C. |
|---|---|
| 25 | 472 |
| 100 | 87.5 |
| 150 | 121 |
| 200 | 2308 |

The water vapor transport rate significantly decreased for samples heated to 100° C. and 150° C. indicating the sealing of pores in the polymer membrane. However, when the Arnitel/Nylon polymers when heated to 200° C. for 10 minutes, WVTR increased to 2308 g/m2.day. The increase in WVTR could be due to the oxidation decomposition of the fabric material as indicated by the color change of the fabric from white to brownish.

Mechanism of Water Vapor Transport (Microporous Polymer Sheets Vs. Monolithic 1 Films)

The water vapor transport rates of microporous membranes and hydrophilic breathable polymer sheets (Arnitel) were compared to determine the best-suited material to make the waste disposal bags for Heat Melt Compactor Application. Microporous membranes exhibited about 10 times higher WVTR rate than for the breathable polymer sheets (Arnitel).

Microporous membranes are hydrophobic and impermeable to liquid water. However, they allow water vapors to diffuse through the micropores less than 1 micron in diameter.

Arnitel type breathable membranes are classified as 'monolithic' sheets without any perforations, holes or micropores. These family of breathable sheets is made using hydrophobic and hydrophilic polymers. Hydrophilic nature of the polymer allows water molecules to absorb, diffuse and desorb on to the other side of the breathable polymer sheet. The absorbed water molecules diffuse through the bulk of the material and are consequently desorbed on the side with the lower relative humidity. The driving force for the diffusion is the difference in partial pressure or concentration gradient of water molecules across the film surface. This mechanism results in lower WVTR in the case of monolithic sheets.

Therefore, it is clear from the WVTR data and the underlining mechanism of microporous and monolithic polymer sheets, microporous membranes will have superior water removal properties from trash than monolithic Arnitel polymer sheets.

A 6 inch by 6-inch Arnitel polymer sheet was pocked with a very fine needle to form micropores forming microporous Arnitel polymer sheets. 50-70 micron diameter pores were made using this process. About 12 pores per square centimeter of the Arnitel polymer sheets were made. The water vapor transport rates can be controlled by the number of perforations or holes per area of the monolithic polymer sheet. These microporous polymer sheets were coated with polyvinyl alcohol polymer mixed with a silver coated copper oxide layer. This multilayer material was used as inner support layers in the multilayer bag. Multilayer storage bags were made from these microporous Arnitel polymer sheets. Water vapor transport of these multilayer storage bags is about 4 times compared to monolithic Arnitel polymer sheets.

Alternatively, small, microporous holes to diameter of 1 micron were made on these monolithic breathable sheets using laser radiation forming microporous polymer sheets.

Testing of Multifunctional Waste Disposal Bag Using HMC Test Chamber

The trash bags filled with trash simulants was placed in the oven. An external liquid nitrogen condenser was used to collect outgoing water vapor from the testing chamber. The amount of water obtained as a function of temperature and pressure was monitored. This task is to demonstrate the capability of the multilayer trash bags to transport water vapor across the bag membrane and the recovery of water with low levels of contaminants that can be treated by the mission water recovery unit for potable use.

The water collected was sent for total organic content and microbial presence analysis. The total organic content (TOC) was 1.06 ppm and no coliform group of bacteria observed in the collected water.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A flexible water vapor permeable, antimicrobial storage bag comprising:
   an outer multifunctional layer and a porous inner support layer,
   wherein the outer multifunctional layer comprises a hydrophilic polymer and an antimicrobial agent,
   wherein the outer multifunctional layer is selected from the group consisting of a coating, and, a sheet,
   wherein the hydrophilic polymer is selected from the group consisting of polyvinyl alcohol and polyvinyl pyrrolidone,
   wherein the antimicrobial is selected from the group consisting of silver doped copper oxide, magnesium hydroxide, copper-doped magnesium hydroxide, silver doped magnesium hydroxide, magnesium oxide, copper doped magnesium oxide, silver doped magnesium oxide, titanium dioxide nanotubes, silver and copper ion exchanged titanium dioxide nanotubes,
   wherein the porous inner support layer comprises a porous polymer sheet selected from the group consisting of polypropylene, nylon, polyester, polyurethane, polyimide, polytetrafluoroethylene, and, polyetherimide,
   wherein the hydrophilic polymer behaves as an adhesive at a temperature higher than about 120 degrees C. and fills up and closes pores in the porous inner support layer,
   wherein inserting a waste material into the flexible, water vapor permeable, antimicrobial storage bag, then sealing the storage bag to encapsulate the waste material, applying vacuum and heating upto 120 degrees centigrade allows recovery of water vapor,
   wherein heating to higher than 120 degrees centigrade configures the flexible, water vapor permeable, antimicrobial storage bag to a substantially water vapor impermeable, antimicrobial product,
   wherein the flexible, water vapor permeable, antimicrobial storage bag has an opening to receive a waste material,
   wherein the substantially water vapor impermeable, antimicrobial product is pressure compressible into a sealed disc,
   wherein the flexible, water vapor permeable, antimicrobial storage bag is impermeable to liquid water at room temperature.

2. A method of providing water vapor recovery, water vapor impermeability and antimicrobial storage of waste material within a storage bag, the method comprising:
   1) preparing a flexible water vapor permeable antimicrobial storage bag;
   2) inserting a waste material;
   3) sealing, applying vacuum and heating the product of step 2) upto 120 degrees centigrade to recover water vapor, and,
   4) heating the product of step 3) to higher than 120 degrees centigrade to create a substantially water vapor impermeable antimicrobial heat treated product,
   wherein heating extracts out water vapor and makes the storage bag substantially water impermeable,
   wherein step 1) comprises coating an outer multifunctional layer onto a porous inner support layer to obtain a multilayer sheet,
   wherein the outer multifunctional layer comprises a hydrophilic polymer and an antimicrobial agent,
   wherein the hydrophilic polymer selected from the group consisting of polyvinyl alcohol and polyvinyl pyrrolidone,
   wherein the antimicrobial is selected from the group consisting of silver doped copper oxide, magnesium hydroxide, copper-doped magnesium hydroxide, silver doped magnesium hydroxide, magnesium oxide, copper doped magnesium oxide, silver doped magnesium oxide, titanium dioxide nanotubes, silver and copper ion exchanged titanium dioxide nanotubes,
   wherein the porous inner support layer comprises a porous polymer sheet selected from the group consisting of polypropylene, nylon, polyester, polyurethane, polyimide, polytetrafluoroethylene, and, polyetherimide,
   wherein the hydrophilic polymer behaves as an adhesive at a temperature higher than about 120 degrees C. and fills up and closes pores in the porous inner support layer,
   wherein the water vapor permeable, antimicrobial storage bag is flexible and comprises an open section to receive waste material.

3. The method of claim 2, further comprising:
   5) compressing the product of step 4) to obtain a compressed, water impermeable, antimicrobial product encapsulating the waste material.

4. A method of providing water vapor recovery, water vapor impermeability and antimicrobial storage of waste material within a storage bag, the method comprising:
   1) preparing a flexible water vapor permeable antimicrobial storage bag;
   2) inserting a waste material;
   3) sealing, applying vacuum and heating the product of step 2) upto 120 degrees centigrade to recover water vapor, and,
   4) heating the product of step 3) to higher than 120 degrees centigrade to create a substantially water vapor impermeable antimicrobial heat treated storage bag,
   wherein heating extracts out water vapor and makes the storage bag water impermeable, wherein step 1) comprises laminating a porous inner support layer with an outer multifunctional sheet to obtain a multilayer sheet, wherein the outer multifunctional sheet comprises a hydrophilic polymer and an antimicrobial agent, wherein the hydrophilic polymer selected from the group consisting of polyvinyl alcohol and polyvinyl pyrrolidone, wherein the antimicrobial is selected from the group consisting of silver doped copper oxide, magnesium hydroxide, copper-doped magnesium hydroxide, silver doped magnesium hydroxide, magnesium oxide, copper doped magnesium oxide, silver doped magnesium oxide, titanium dioxide nanotubes, silver and copper ion exchanged titanium dioxide nanotubes, wherein the porous inner support layer of step b) comprises a porous polymer sheet selected from the group consisting of polypropylene, nylon, polyester, polyurethane, polyimide, polytetrafluoroethylene, and, polyetherimide, wherein the hydrophilic polymer behaves as an adhesive at a temperature higher than about 120 degrees C. and fills up and closes pores in the porous inner support layer, wherein the water vapor permeable, antimicrobial storage bag is flexible and comprises an open section to receive waste material.

5. The method of claim 4, further comprising:
5) compressing the product of step 4) to obtain a compressed, water impermeable, antimicrobial product encapsulating the waste material.

* * * * *